(12) United States Patent
Teshigawara

(10) Patent No.: US 12,198,233 B2
(45) Date of Patent: Jan. 14, 2025

(54) NUCLEAR MEDICINE DIAGNOSIS APPARATUS AND NUCLEAR MEDICINE DIAGNOSIS METHOD

(71) Applicant: CANON MEDICAL SYSTEMS CORPORATION, Tochigi (JP)

(72) Inventor: Manabu Teshigawara, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 329 days.

(21) Appl. No.: 17/656,957

(22) Filed: Mar. 29, 2022

(65) Prior Publication Data

US 2022/0319068 A1    Oct. 6, 2022

(30) Foreign Application Priority Data

Mar. 30, 2021    (JP) ................................. 2021-058499

(51) Int. Cl.
*G06T 11/00* (2006.01)
*A61B 6/00* (2024.01)
(Continued)

(52) U.S. Cl.
CPC ............ *G06T 11/005* (2013.01); *A61B 6/037* (2013.01); *A61B 6/5282* (2013.01);
(Continued)

(58) Field of Classification Search
CPC ....... G06T 11/005; G06T 7/11; G06T 7/0012; G06T 2207/10104; G06T 2207/20076;
(Continued)

(56) References Cited

U.S. PATENT DOCUMENTS

2006/0050845 A1*  3/2006  Juni ..................... G01T 1/1615
                                                                 378/51
2012/0290519 A1    11/2012  Fontaine et al.
(Continued)

OTHER PUBLICATIONS

Extended European Search Report issued Oct. 26, 2022 in European Patent Application No. 22165423.9, 7 pages.
(Continued)

*Primary Examiner* — Pinalben Patel
(74) *Attorney, Agent, or Firm* — Oblon, McClelland, Maier & Neustadt, L.L.P.

(57) ABSTRACT

A nuclear medicine diagnosis apparatus according to an embodiment includes a processing circuit. The processing circuit is configured: to obtain coincidence data including a direct incidence event to a gamma ray detector and a scattering event in a subject; to obtain an electron density function of the subject and geometric information of the gamma ray detector; to estimate a first probability value corresponding to the direct incidence event in the subject and a second probability value corresponding to the scattering event, based on one or both of the electron density function and the geometric information; and to reconstruct a Positron Emission Tomography (PET) image based on the first probability value, the second probability value, and the coincidence data. The processing circuit is configured to reconstruct the PET image based on a system matrix that is based on the first probability value and the second probability value.

6 Claims, 10 Drawing Sheets

(51) Int. Cl.
*A61B 6/03* (2006.01)
*G06T 7/00* (2017.01)
*G06T 7/11* (2017.01)

(52) U.S. Cl.
CPC .............. *G06T 7/0012* (2013.01); *G06T 7/11* (2017.01); *G06T 2207/10104* (2013.01); *G06T 2207/20076* (2013.01); *G06T 2207/30004* (2013.01)

(58) Field of Classification Search
CPC .......... G06T 2207/30004; A61B 6/037; A61B 6/5282
See application file for complete search history.

(56) References Cited

U.S. PATENT DOCUMENTS

| | | | | |
|---|---|---|---|---|
| 2018/0075629 | A1* | 3/2018 | Zhou | G06T 11/006 |
| 2018/0144514 | A1* | 5/2018 | Zhou | G06T 7/0012 |
| 2019/0209116 | A1* | 7/2019 | Sjöstrand | G16H 50/30 |
| 2023/0333269 | A1* | 10/2023 | Li | G01T 1/2985 |

OTHER PUBLICATIONS

Schaar et al., "Modelling of Scatter in the System Matrix for 3D PET Image Reconstruction: a Comparative Study", IEEE, Oct. 26, 2019, pp. 1-2, XP 033747909.

Markiemicz et al., "Towards an Accurate Voxel-Based Analytic Unified Scatter and Attenuation System Model for 3D PET", IEEE, vol. 4, Oct. 16, 2004, pp. 2199-2203, XP 010822619.

Werling et al., "Fast Implementation of the Single scatter simulation algorithm and its use in iterative image reconstruction of PET data", physics in Medicine and Biology, vol. 47, No. 16, Aug. 2002, pp. 2947-2960, XP002318421.

Combined Chinese Office Action and Search Report issued May 27, 2024 in Chinese Patent Application No. 202210319855.5 (with English Translation of Category of Cited Documents), 8 pages.

Office Action issued Aug. 28, 2024, in corresponding Japanese Patent Application No. 2021-058499 with English translation, 6 pages.

* cited by examiner

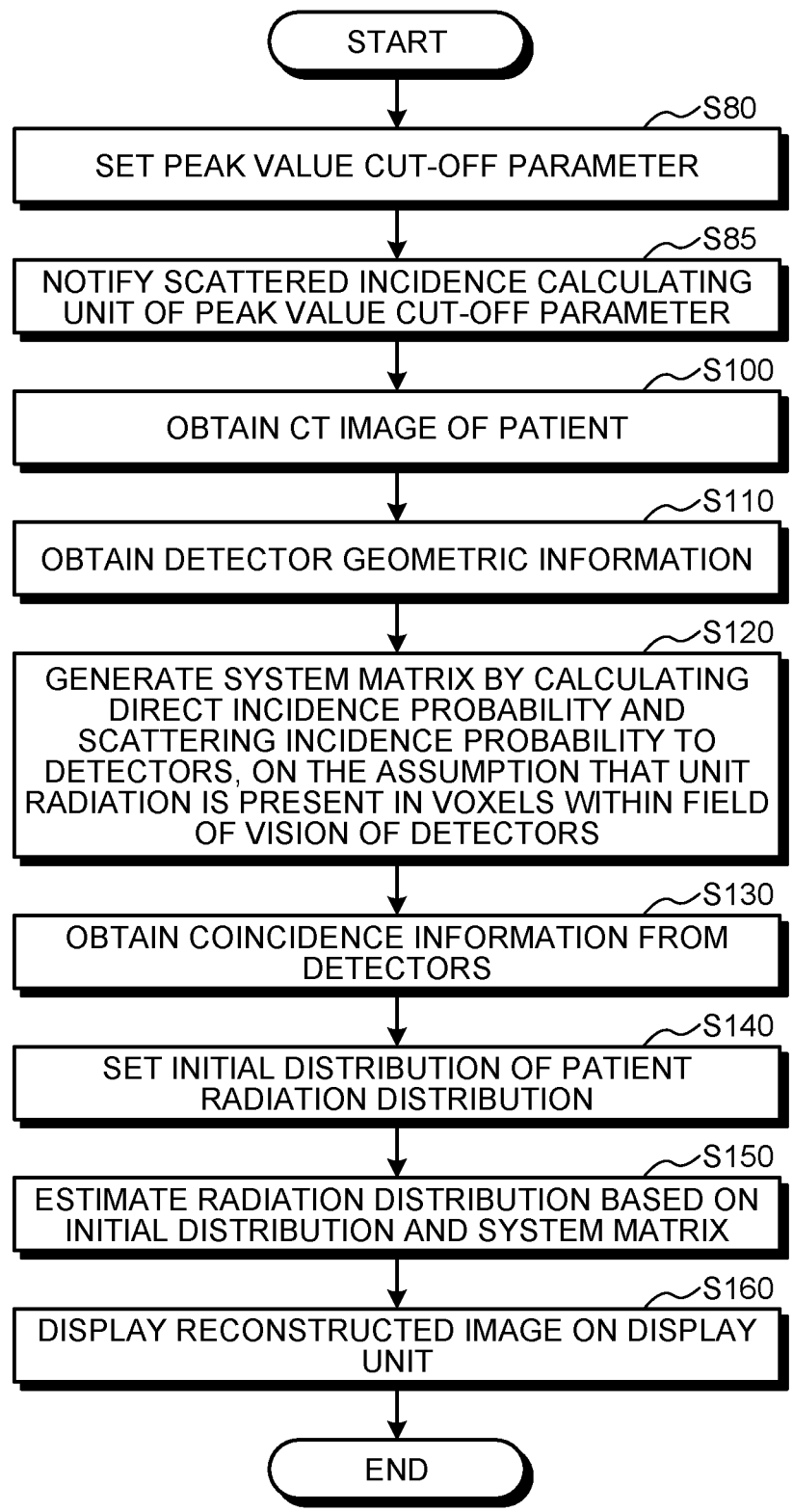

NUCLEAR MEDICINE DIAGNOSIS APPARATUS AND NUCLEAR MEDICINE DIAGNOSIS METHOD

CROSS-REFERENCE TO RELATED APPLICATIONS

This application is based upon and claims the benefit of priority from Japanese Patent Application No. 2021-058499, filed on Mar. 30, 2021; the entire contents of which are incorporated herein by reference.

FIELD

Embodiments described herein relate generally to a nuclear medicine diagnosis apparatus, and a nuclear medicine diagnosis method.

BACKGROUND

Many of the Positron Emission Tomography (PET) apparatuses at present are configured to reconstruct an image by estimating a radiation distribution inside a subject, based on direct incidence events which are events of detecting gamma rays becoming incident to a detector without being scattered on the inside of the subject. Generally speaking, although an algorithm used for the image reconstruction has a scattered ray correcting function, the scattered ray correction is, in many situations, carried out on scatterings of single scattering at most. When the scattered ray correction is carried out on single scattering at most, however, there is a possibility that image quality may be degraded.

Further, to precisely perform a scattered ray correction that can eliminate low-energy gamma ray detection events having gone through multiple scatterings, it may be required to use scintillators having a large light emission amount and a large number of light receiving cells that correspond to the scintillators having the large light emission amount.

In addition, for example, when a high temporal resolution is sought after in Time Of Flight (TOF)-PET, scintillators are required to be short-time light emission scintillators, whereas the optical detectors are required to have a quick response and a short-time recovery in each cell. However, scintillators that satisfy these conditions can be expensive.

BRIEF DESCRIPTION OF THE DRAWINGS

FIG. 10 is a flowchart for explaining a procedure in a process performed by a nuclear medicine diagnosis apparatus according to the fourth embodiment.

DETAILED DESCRIPTION

A nuclear medicine diagnosis apparatus provided in one aspect of the present disclosure includes a processing circuit. The processing circuit is configured: to obtain coincidence data including a direct incidence event to a gamma ray detector and a scattering event in a subject; to obtain an electron density function of the subject and geometric information of the gamma ray detector; to estimate a first probability value corresponding to the direct incidence event in the subject and a second probability value corresponding to the scattering event, based on one or both of the electron density function and the geometric information; and to reconstruct a PET image based on the first probability value, the second probability value, and the coincidence data. The processing circuit is configured to reconstruct the PET image based on a system matrix that is based on the first probability value and the second probability value.

Exemplary embodiments of a nuclear medicine diagnosis apparatus, a medical image processing device, a nuclear medicine diagnosis method, and a program will be explained in detail below, with reference to the accompanying drawings.

First Embodiment

Figure 1:
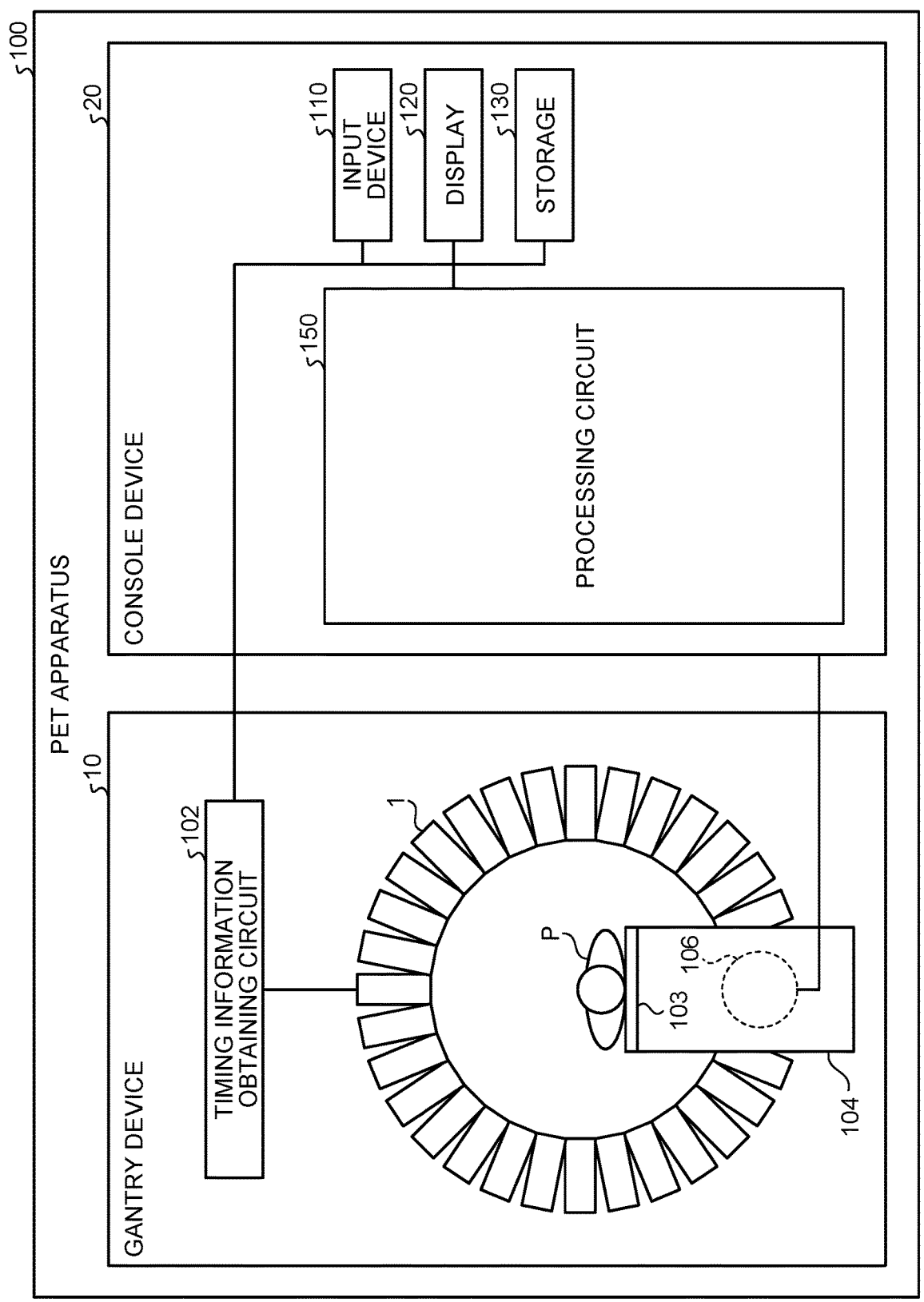
FIG. 1 is a diagram illustrating an example of a nuclear medicine diagnosis apparatus according to an embodiment.

FIG. 1 is a diagram illustrating a configuration of a PET apparatus 100 serving as a nuclear medicine diagnosis apparatus according to an embodiment. As illustrated in FIG. 1, the PET apparatus 100 according to the embodiment includes a gantry device 10 and a console device 20 serving as a medical image processing device. The gantry device 10 includes detectors 1, a timing information obtaining circuit 102, a tabletop 103, a table 104, and a table driving unit 106.

The detectors 1 are detectors configured to detect radiation by detecting scintillation photons (fluorescent light) representing light that is re-released when a substance in an excited state transitions back into a ground state as a result of an interaction between annihilation gamma rays released from positrons in an examined subject (hereinafter, "patient") P and light emitting bodies (scintillators). The detectors 1 are configured to detect radiation energy information of the annihilation gamma rays released from the positrons inside the patient P. The plurality of detectors 1 are arranged so as to surround the patient P in a ring formation, while forming a plurality of detector blocks, for example.

An example of a specific configuration of the detectors 1 may be detectors of an Anger type using a photon counting method and including, for example, scintillators, optical detecting elements, and a light guide. In other words, each of the pixels included in the detectors 1 has a scintillator and an optical detecting element configured to detect generated scintillation photons.

The scintillators are configured to convert the annihilation gamma rays that have become incident thereto after being released from the positrons inside the patient P, into scintillation photons (or optical photons) and to output the scintillation photons. The scintillators are formed with scintillator crystals that are suitable for a TOF measuring process or an energy measuring process, such as those of Lanthanum Bromide (LaBr3), Lutetium Yttrium Oxyorthosilicate (LYSO), Lutetium Oxyorthosilicate (LSO), Lutetium Gadolinium Oxyorthosilicate (LGSO), or Bismuth Germanium Oxide (BGO), for example, and are arranged two-dimensionally, for example.

As the optical detecting elements, for example, Silicon Photomultipliers (SiPMs) or photomultiplier tubes may be used. Each of the photomuplier tubes includes: a photocathode configured to receive the scintillation photons and to generate photoelectrons; multi-stage dynodes configured to provide an electric field for accelerating the generated photoelectrons; and an anode through which electrons flow out. The photomultiplier tubes are configured to multiply the scintillation photons output from the scintillators and to convert the multiplied result into electrical signals.

Further, by employing the timing information obtaining circuit 102, the gantry device 10 is configured to generate count information from output signals of the detectors 1 and to store the generated count information into a storage 130 of the console device 20. Further, the detectors 1 are divided in the plurality of blocks and are provided with the timing information obtaining circuit 102.

The timing information obtaining circuit 102 is configured to convert the output signals from the detectors 1 into digital data and to generate the count information. The count information includes detection positions of the annihilation gamma rays, energy values, and detection times. For example, the timing information obtaining circuit 102 identifies a plurality of optical detecting elements that converted scintillation photons into electrical signals at mutually the same time. Further, the timing information obtaining circuit 102 identifies scintillator numbers (P) indicating the positions of the scintillators to which the annihilation gamma rays became incident. As for a means for identifying the positions of the scintillators to which the annihilation gamma rays became incident, it is possible to identify the positions by performing a center-of-gravity calculation based on the positions of the optical detecting elements and intensities of the electrical signals. Further, when the element sizes of the scintillators and the optical detecting elements correspond with each other, the scintillators corresponding to the optical detecting elements from which outputs were obtained may be identified as the positions of the scintillators to which the annihilation gamma rays became incident.

Further, the timing information obtaining circuit 102 is configured to identify energy values (E) of the annihilation gamma rays that became incident to the detectors 1, through an integral calculation on intensities of the electrical signals output from the optical detecting elements. Further, the timing information obtaining circuit 102 is configured to identify detection times (T) at which the scintillation photons from the annihilation gamma rays were detected by the detectors 1. The detection times (T) may be absolute times or elapsed time periods since the start of the imaging process. As explained herein, the timing information obtaining circuit 102 is configured to generate the count information including the scintillator numbers (P), the energy values (E), and the detection times (T).

In this situation, the timing information obtaining circuit 102 is realized by using, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The timing information obtaining circuit 102 is an example of a timing information obtaining unit.

The tabletop 103 is a bed on which the patient P is placed and is arranged over the table 104. The table driving unit 106 is configured to move the tabletop 103 under control of a table controlling function 150$k$ of a processing circuit 150. For example, the table driving unit 106 is configured to move the patient P to the inside of an imaging opening of the gantry device 10, by moving the tabletop 103.

Upon receipt of an operation performed by an operator on the PET apparatus 100, the console device 20 is configured to control imaging of a PET image and to reconstruct the PET image by using the count information acquired by the gantry device 10. As illustrated in FIG. 1, the console device 20 includes the processing circuit 150, an input device 110, a display 120, and the storage 130. In this situation, functional units included in the console device 20 are connected together via a bus. Details of the processing circuit 150 will be explained later.

The input device 110 is a mouse, a keyboard, and/or the like used by the operator of the PET apparatus 100 for inputting various types of instructions and various types of settings and is configured to transfer the input various types of instructions and various types of settings to the processing circuit 150. For example, the input device 110 may be used for inputting an instruction to start imaging processes.

The display 120 is a monitor or the like referenced by the operator and is configured, under control of the processing circuit 150, to display a respiratory waveform and the PET image of the patient and to display a Graphical User Interface (GUI) used for receiving the various types of instructions and the various types of settings from the operator.

The storage 130 is configured to store therein various types of data used in the PET apparatus 100. For example, the storage 130 is configured by using a memory and may be, in an example, realized by using a semiconductor memory element such as a Random Access Memory (RAM) or a flash memory, or a hard disk, an optical disk, or the like. The storage 130 is configured to store therein the count information which is the information in which the scintillator numbers (P), the energy values (E), and the detection times (T) are kept in correspondence with one another, coincidence information in which coincidence numbers serving as serial numbers of pieces of coincidence information are kept in correspondence with sets of count information, the reconstructed PET image, and the like.

Next, a background of the embodiment will be explained.

Many of the PET apparatuses at present are, in principle, configured to reconstruct an image by estimating a radiation distribution inside a subject, based on direct incidence events which are events of detecting gamma rays becoming incident to a detector without being scattered on the inside of the subject. Generally speaking, although an algorithm used for the image reconstruction has a scattered ray correcting function, the scattered ray correction is, in many situations, carried out on scatterings of single scattering at most. When the scattered ray correction is carried out on single scattering at most, however, there is a possibility that image quality may be degraded.

Figure 2:
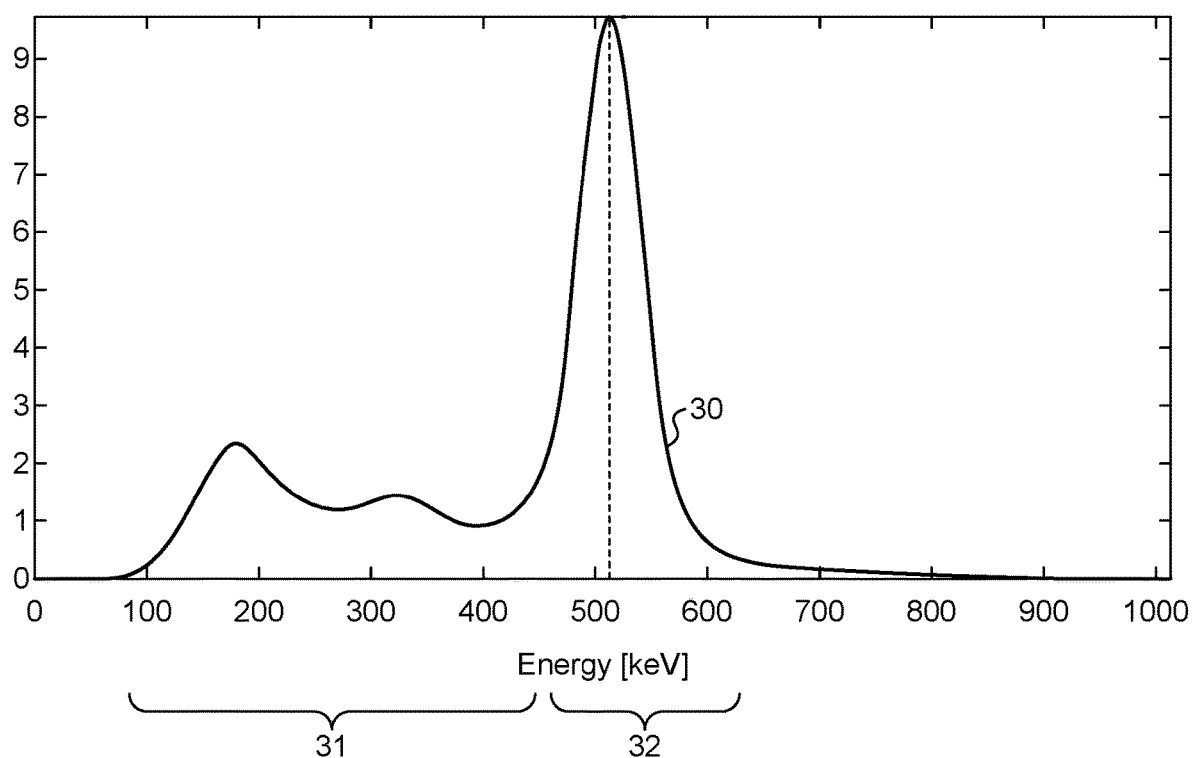
FIG. 2 is a chart for explaining a background of the embodiment.

For example, in FIG. 2, the curve 30 is a graph in which signal intensities of gamma rays becoming incident to detectors is expressed a function of energy. The region 32 is an energy region corresponding to direct incidence events and single scattering events. In contrast, the region 31 is an energy region corresponding to multiple scatterings. In comparison to the events in the region 32 being the energy region corresponding to the direct incidence events and the single scattering events, the events in the region 31 being the energy region corresponding to the multiple scatterings have lower signal intensities, and because a plurality of types of events are superimposed together, it is more difficult to correct scattering characteristics.

As a method for precisely performing a scattered ray correction that can eliminate low-energy gamma ray detection events having gone through multiple scatterings, a possible method involves preparing scintillators having a large light emission amount and being used for precisely measuring incidence energy, as well as a large number of light receiving cells that correspond to the scintillators having the large light emission amount. In this situation, for example, when SiPMs are used as optical detectors to convert scintillation photons into electrical signals, it is required to use a large number (thousands to tens of thousands) of light receiving cells so as to correspond to the scintillation with the large light emission amount.

In addition, for example, when a high temporal resolution is sought after in Time Of Flight (TOF)-PET, scintillators are required to be short-time light emission scintillators, whereas the optical detectors are required to have a quick response and a short-time recovery in each cell. Furthermore, at a stage subsequent to the optical detectors, it is necessary to provide an electronic circuit configured to calculate energy based on signals. In many situations, it would be required to develop an ASIC suitable for the apparatus in use.

As explained above, in TOF-PET, to correct the scattered rays including the multiple scatterings, an energy measuring system included in the single PET apparatus 100 could be complicated and could have an extremely large number of channels. Further, because operations of the channels uniquely vary among the channels, achieving measurement precision by correcting the variation in the operations would require implementing a complicated procedure at the time of actual use. In addition, scintillators satisfying both of the conditions required of TOF-PET at the same time such as a large light emission amount and short light emission time would be expensive.

Accordingly, the capability to effectively correct multiple scattering events without using the scintillators that satisfy the conditions of both a large light emission amount and short light emission time at the same time will significantly reduce design-related restrictions on PET apparatuses imposed by the energy measuring system.

In view of the background described above, the nuclear medicine diagnosis apparatus according to the embodiment is configured to use a new method for correcting multiple scattering events in a PET apparatus. More specifically, the nuclear medicine diagnosis apparatus according to the embodiment is configured: to obtain an electron density function of a subject and geometric information of the gamma ray detectors; to estimate, based on the obtained pieces of data, a first probability value corresponding to direct incidence events and a second probability value corresponding to scattering events including multiple scattering events; and to reconstruct a PET image based on the estimated probability values and coincidence data.

As a result, it is possible to enhance image quality or to significantly reduce design-related restrictions on the PET apparatus imposed by the energy measuring system. For example, it becomes possible to design PET apparatuses by using scintillators less expensive than those currently used and to enhance capabilities of the PET apparatuses.

Figure 3:
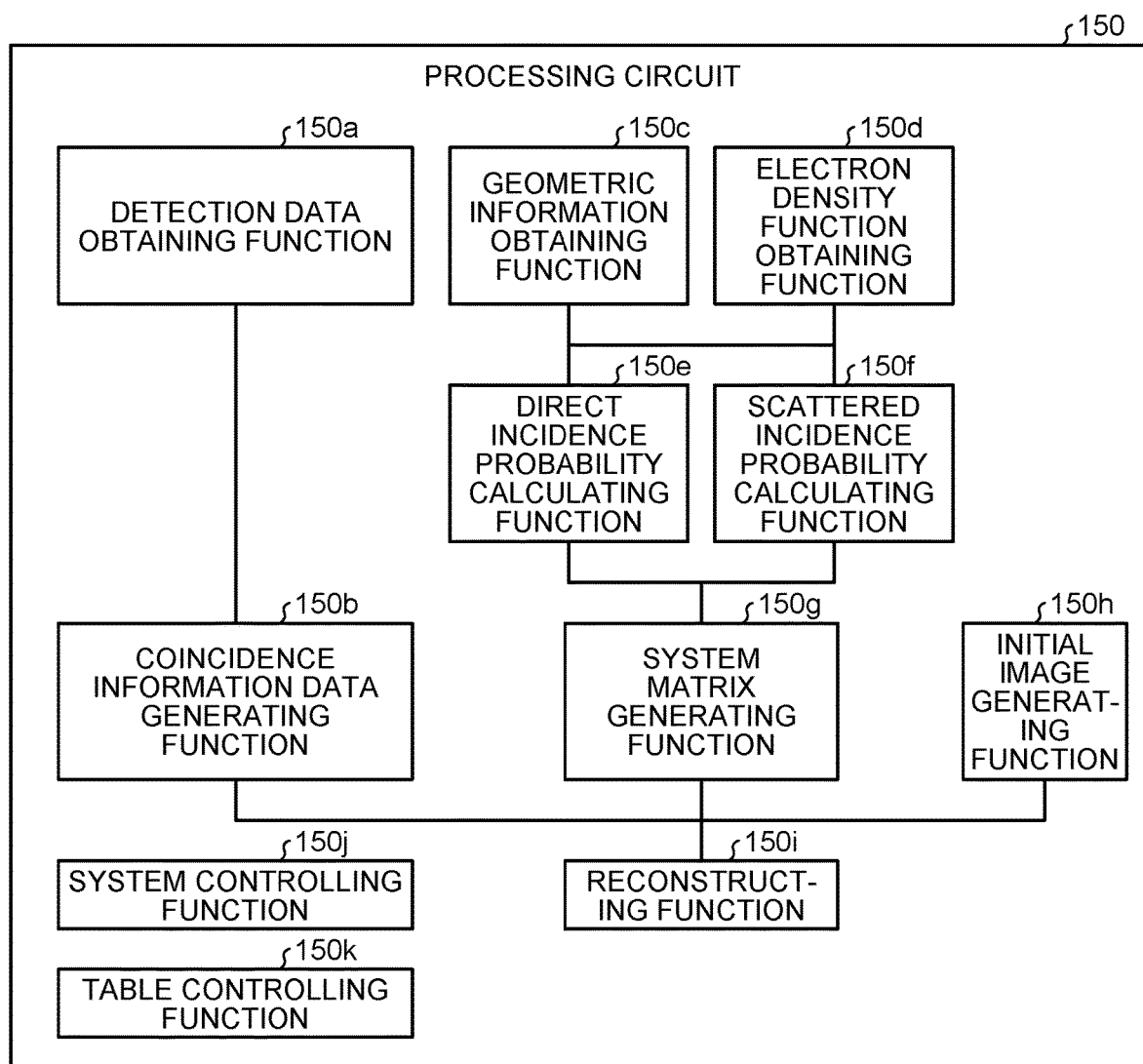
FIG. 3 is a diagram for explaining a processing circuit according to a first embodiment.
Figure 4:
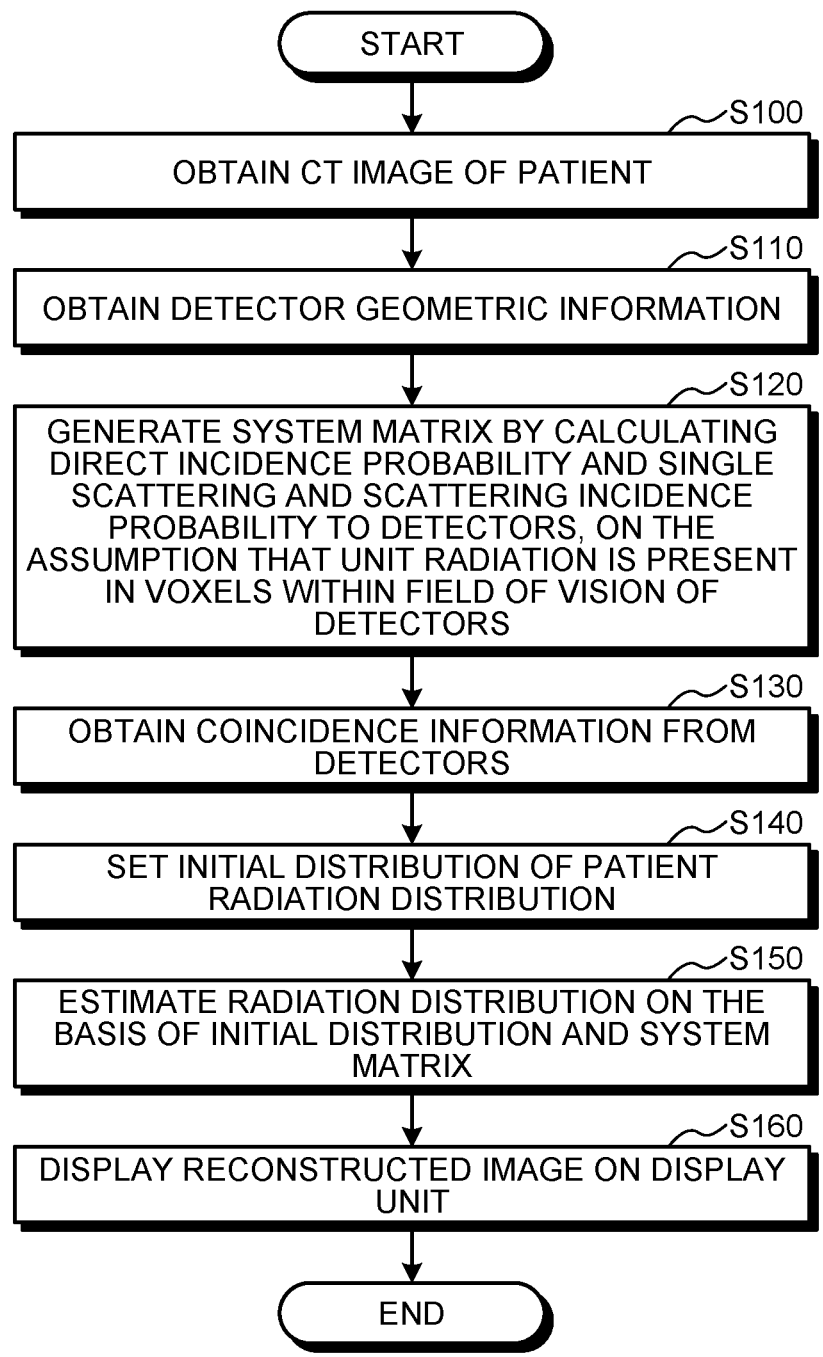
FIG. 4 is a flowchart for explaining a procedure in a process performed by a nuclear medicine diagnosis apparatus according to the first embodiment.

Next, the PET apparatus 100 according to a first embodiment will be explained in detail, with reference to FIGS. 3 and 4. FIG. 3 is a diagram for explaining a configuration of the processing circuit 150 included in the PET apparatus 100 according to the first embodiment. FIG. 4 is a flowchart for explaining a process performed by the PET apparatus 100 according to the embodiment.

As illustrated in FIG. 3, in the first embodiment, the processing circuit 150 includes a detection data obtaining function 150a, a coincidence information data generating function 150b, a geometric information obtaining function 150c, an electron density function obtaining function 150d, a direct incidence probability calculating function 150e, a scattered incidence probability calculating function 150f, a system matrix generating function 150g, an initial image generating function 150h, a reconstructing function 150i, a system controlling function 150j, and the table controlling function 150k. The functions other than the system controlling function 150j and the table controlling function 150k will be explained in detail later, with reference to FIG. 4.

In the embodiment, processing functions performed by the detection data obtaining function 150a, the coincidence information data generating function 150b, the geometric information obtaining function 150c, the electron density function obtaining function 150d, the direct incidence probability calculating function 150e, the scattered incidence probability calculating function 150f, the system matrix generating function 150g, the initial image generating function 150h, the reconstructing function 150i, the system controlling function 150j, and the table controlling function 150k are stored in the storage 130 in the form of computer-executable programs. The processing circuit 150 is a processor configured to realize the functions corresponding to the programs, by reading and executing the programs from the storage 130. In other words, the processing circuit 150 that has read the programs has the functions illustrated within the processing circuit 150 in FIG. 3.

Further, although the example is explained with reference to FIG. 3 in which the single processing circuit (i.e., the processing circuit 150) realizes the processing functions performed by the detection data obtaining function 150a, the coincidence information data generating function 150b, the geometric information obtaining function 150c, the electron density function obtaining function 150d, the direct incidence probability calculating function 150e, the scattered incidence probability calculating function 150f, the system matrix generating function 150g, the initial image generating function 150h, the reconstructing function 150i, the system controlling function 150j, and the table controlling function 150k, it is also acceptable to structure the processing circuit 150 by combining together a plurality of independent processors so that the functions are realized as a result of the processors executing the programs. In other words, each of the abovementioned functions may be structured as a program, so that the single processing circuit (i.e., the processing circuit 150) executes the programs. In another example, one or more specific functions may be installed in a dedicated and independent program executing circuit.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors are configured to realize the functions by reading and executing the programs saved in the storage 130.

The abovementioned configuration is not limited to the processing circuit 150 illustrated in FIG. 3. It is possible to apply the same configuration to any of the processing circuits 150 illustrated in FIGS. 5, 7, and 9 explained later.

In FIG. 3, the detection data obtaining function 150a, the coincidence information data generating function 150b, and the initial image generating function 150h are examples of the first obtaining unit. Further, the geometric information obtaining function 150c and the electron density function obtaining function 150d are examples of the second obtaining unit. The direct incidence probability calculating function 150e, the scattered incidence probability calculating function 150f, and the system matrix generating function 150g are examples of the estimating unit. The reconstructing function 150i is an example of the reconstructing unit. The system controlling function 150j and the table controlling function 150k are examples of a controlling unit.

By employing the system controlling function 150j the processing circuit 150 is configured to control the entirety of the PET apparatus 100 by controlling the gantry device 10 and the console device 20. For example, by employing the system controlling function 105j, the processing circuit 150 is configured to control imaging processes of the PET apparatus 100.

By employing the table controlling function 150k, the processing circuit 150 is configured to control the table driving unit 106.

Next, while explaining the functions included in the processing circuit 150 with reference to FIG. 4, a flow in a process performed by the PET apparatus 100 according to the first embodiment will be explained. At step S100, by employing the electron density function obtaining function 150d, the processing circuit 150 obtains an electron density function of the patient. In an example, by employing the electron density function obtaining function 150d, the processing circuit 150 obtains a CT image of the patient as the electron density function. In an example, by employing the electron density function obtaining function 150d, the processing circuit 150 obtains the CT image of the patient acquired as a result of imaging the patient with a CT apparatus (not illustrated), as the electron density function of the patient. Further, in another example, the nuclear medicine diagnosis apparatus according to the embodiment may be a PET-CT apparatus having a function of a CT apparatus, so that the processing circuit 150 obtains, by employing the electron density function obtaining function 150d, a CT image of the patient acquired as a result of a CT imaging process performed on the patient by the PET-CT apparatus.

In this situation, data expressing the electron density function of the patient does not necessarily have to be data obtained by performing a CT imaging process. In an example, the data expressing the electron density function of the patient may be a magnetic resonance image. For example, by employing the electron density function obtaining function 150d, the processing circuit 150 may obtain, as the electron density function of the patient, the magnetic resonance image acquired by imaging the patient while using a Magnetic Resonance Imaging (MRI) apparatus (not illustrated) and performing a segmentation process, for example.

As explained above, at step S100, the PET apparatus 100 according to the embodiment obtains, by employing the electron density function obtaining function 150d, the electron density function of the patient, separately from the data obtained by performing the PET imaging process. As a result, the processing circuit 150 is able to obtain the information serving as a basis for estimating multiple scatterings of the gamma rays. As compared to the existing method, the precision level of the estimation of the multiple scatterings at the subsequent steps is enhanced.

After that, at step S110, by employing the geometric information obtaining function 150c, the processing circuit 150 obtains geometric information of the detectors 1 that are the gamma ray detectors. In this situation, the geometric information of the detectors 1 denotes information about relative positional relationships among the detectors 1 and information about a positional relationship between the detectors 1 and the patient P. In an example, by employing the geometric information obtaining function 150c, the processing circuit 150 is configured to obtain the information about the relative positional relationships among the detectors 1, by obtaining, from the storage 130, the information about the relative positional relationships among the detectors 1 stored in the storage 130 in advance. Further, by employing the geometric information obtaining function 150c, the processing circuit 150 is configured to obtain the information about the positional relationship between the detectors 1 and the patient P, by obtaining the position of the patient P via the table driving unit 106. In this situation, for example, the process at step S110 and the process at step S100 may be performed in the reverse order. Similarly, in FIG. 10 (explained later) also, the process at step S110 and the process at step S100 may be performed in the reverse order.

Subsequently, at step S120, by employing the direct incidence probability calculating function 150e, the processing circuit 150 calculates the first probability value indicating a probability of the gamma rays directly becoming incident to the detectors 1, based on the electron density of the patient obtained by the electron density function obtaining function 150d at step S100 and the geometric information of the detectors 1 obtained by the geometric information obtaining function 150c at step S110. In this situation, the phrase "the gamma rays directly become incident to the detectors 1" denotes that the number of times of scattering where a pair of generated gamma rays is scattered en route before reaching the detectors 1 is zero.

In this situation, at step S120, the processing circuit 150 performs the calculation on the assumption that unit radiation is emitted from each of the voxels set in a field of vision of the detectors. Further, an actual radiation amount with respect to each of the voxels will be estimated at step S150.

By employing the direct incidence probability calculating function 150e, the processing circuit 150 is configured to estimate the first probability value corresponding to the direct incidence events in the patient, on the assumption that unit radiation is present in the voxels within the field of vision of the detectors, based on one or both of the electron density function of the patient and the geometric information of the gamma ray detectors. In an example, by employing the direct incidence probability calculating function 150e, the processing circuit 150 is configured to calculate the first probability value indicating a direct incidence probability to each of the detectors 1, on the assumption that unit radiation is present in the voxels within the field of vision of the detectors, based on one or both of the electron density function of the patient and the geometric information of the gamma ray detectors, by using, for example, a radiative transfer equation, a Monte Carlo simulation, a neural network, or the like.

Further, by employing the scattered incidence probability calculating function 150f, the processing circuit 150 is configured to calculate a probability of the gamma rays becoming incident to the detectors 1 after being scattered, based on the electron density of the patient obtained by the electron density function obtaining function 150d at step S100 and the geometric information of the detectors 1 obtained by the geometric information obtaining function 150c at step S110. In this situation, "after being scattered" includes both becoming incident after single scattering and becoming incident after multiple scatterings.

In other words, by employing the scattered incidence probability calculating function 150f, the processing circuit 150 is configured to estimate the second probability value corresponding to scattering events including multiple scattering events in the patient, on the assumption that unit radiation is present in the voxels within the field of vision of the detectors, based on one or both of the electron density function of the patient and the geometric information of the gamma ray detectors. More specifically, by employing the scattered incidence probability calculating function 150f, the processing circuit 150 is configured to calculate a scattered incidence probability of the detectors 1 on the assumption that unit radiation is present in the voxels within the field of vision of the detectors, by using, for example, a radiative transfer equation, a Monte Carlo simulation, a neural network, or the like.

Subsequently, by employing the system matrix generating function 150g, the processing circuit 150 is configured to generate a system matrix H, based on the direct incidence probability calculated by the direct incidence probability calculating function 150e and the scattered incidence probability calculated by the scattered incidence probability calculating function 150f. In this situation, the system matrix H is a matrix in which the elements are expressed as $H_{ij}$, where the letter "i" denotes an i-th Line Of Response (LOR), whereas the letter "j" denotes a j-th voxel.

In this situation, in the first embodiment and a second embodiment, effects of the scatterings are expressed as a scattering matrix while being incorporated in the system matrix. In contrast, a third embodiment is different in that the effects of the scatterings are expressed as a scattering term separate from the system matrix, by using a shifted Poisson model or the like, for example.

At step S130, the processing circuit 150 obtains the count information from the timing information obtaining circuit 102. More specifically, by employing the detection data obtaining function 150a, the processing circuit 150 obtains detection data of the gamma rays from the timing information obtaining circuit 102. In this situation, the detection data of the gamma rays obtained from the timing information obtaining circuit 102 by the processing circuit 150 while employing the detection data obtaining function 150a is, for example, the count information including the scintillator numbers (P), the energy values (E), and the detection times (T). The count information includes both data derived from the direct incidence and data derived from the scattered incidence.

Subsequently, by employing the coincidence information data generating function 150b, the processing circuit 150 generates coincidence information data, based on the count information obtained by the detection data obtaining function 150a.

In other words, at step S130, by employing the detection data obtaining function 150a and the coincidence information data generating function 150b, the processing circuit 150 obtains the coincidence data including the direct incidence events to the gamma ray detectors 1 and the scattering events in the patient P.

After that, at step S140, by employing the initial image generating function 150h, the processing circuit 150 sets an initial distribution of a patient radiation distribution. In an example, by employing the initial image generating function 150h, the processing circuit 150 generates an average radiation distribution by performing an averaging operation on PET images of a plurality of patients and sets the average radiation distribution as the initial distribution. In another example, by employing the initial image generating function 150h, the processing circuit 150 may set, with respect to the CT image of the patient obtained at step S100, an initial distribution in which a certain level of radiation is distributed in locations where the electron density is equal to or higher than a certain threshold value, whereas no radiation is distributed in the other locations. In yet another example, by employing the initial image generating function 150h, the processing circuit 150 may determine, as the initial distribution of the patient radiation distribution, an electron density distribution calculated from the CT image of the patient obtained at step S100.

Subsequently, at step S150, by employing the image reconstructing function 150i, the processing circuit 150 generates a reconstructed image through reconstruction of a PET image, by estimating the radiation distribution of the patient based on the initial distribution of the patient radiation set at step S140, the system matrix generated at step S120, and the coincidence data obtained at step S130. In other words, by employing the image reconstructing function 150i, the processing circuit 150 is configured to reconstruct the PET image based on the initial distribution of the patient radiation set at step S140, the first probability value and the second probability value estimated at step S120, and the coincidence data obtained at step S130. In an example, by employing the image reconstructing function 150i, the processing circuit 150 reconstructs the PET image based on the initial distribution of the patient radiation set at step S140, the system matrix based on the first probability value and the second probability value estimated at step S120, and the coincidence data obtained at step S130. In an example, by employing the image reconstructing function 150i, the processing circuit 150 generates the reconstructed image by estimating, while using a maximum likelihood method, a neural network, or the like, the radiation distribution of the patient that reproduces the coincidence information obtained at step S130, based on the initial distribution of the patient radiation set at step S140 and the system matrix generated at step S120.

Subsequently, at step S160, by employing the system controlling function 150j, the processing circuit 150 causes the display 120 to display the reconstructed image generated at step S150.

As explained above, in the first embodiment, the electron density function of the patient and the geometric information of the gamma ray detectors are obtained, so that the first probability value corresponding to the direct incidence events and the second probability value corresponding to the scattering events including multiple scattering events are estimated based on the obtained pieces of data, so as to reconstruct the PET image based on the estimated probability values and the coincidence data. According to the first embodiment, it is possible to structure the PET apparatus capable of performing the imaging and reconstructing processes that make use of the patient information included in the scattered rays. Further, because the electron density function of the patient and the geometric information of the gamma ray detectors are present, it is not requisite to have an expensive energy measuring circuit installed in the PET apparatus for the purpose of measuring the energy of the detected gamma rays. The degree of freedom in design is thus enhanced.

In an example, it is possible to manufacture a nuclear medicine diagnosis apparatus capable of obtaining high-quality PET images by using less expensive scintillators than those conventionally used. Further, in another example, the method according to the embodiment makes it possible to adopt scintillators having characteristics advantageous for TOF functions (e.g., an extremely quick response to incidence of gamma rays although the light emission amount is small). The range of selection for the scintillators is thus widened.

In addition, in the method according to the first embodiment, the generated system matrix coherently handles the scattering process and the attenuation process. It is therefore not necessary to manually tune the relative intensities between the scattering process and the attenuation process, unlike in conventional methods. Further, in the method according to the first embodiment, because the image is reconstructed by processing all the events including the multiple scatterings, it is possible to obtain the image in which statistical noise is suppressed. In addition, when the method according to the first embodiment is used, imaging with reduced radiation exposure is also expected to be possible, due to an increase in the amount of a radioactive drug to be administered.

Second Embodiment

Next, the second embodiment will be explained with reference to FIGS. 5 and 6. In the first embodiment, the example was explained in which the electron density function of the patient and the geometric information of the gamma ray detectors are obtained so that the system matrix is estimated based on the obtained pieces of data, so as to reconstruct the PET image based on the estimated system matrix. The second embodiment has the same configuration where the electron density function of the patient and the geometric information of the gamma ray detectors are obtained so that a system matrix is calculated based on the obtained pieces of data; however, in detail, the system matrix is calculated by using a procedure different from that in the first embodiment. In other words, in the system matrix, the part contributed by the direct incidence is a part not dependent on the shape of the electron density function of the patient. Accordingly, in the system matrix, the part contributed by the direct incidence is separately calculated by the processing circuit, in advance, so that a system matrix is generated by subsequently adding thereto a part contributed by the scattered incidence. As a result, it is possible to simplify the calculation of the system matrix.

Figure 5:
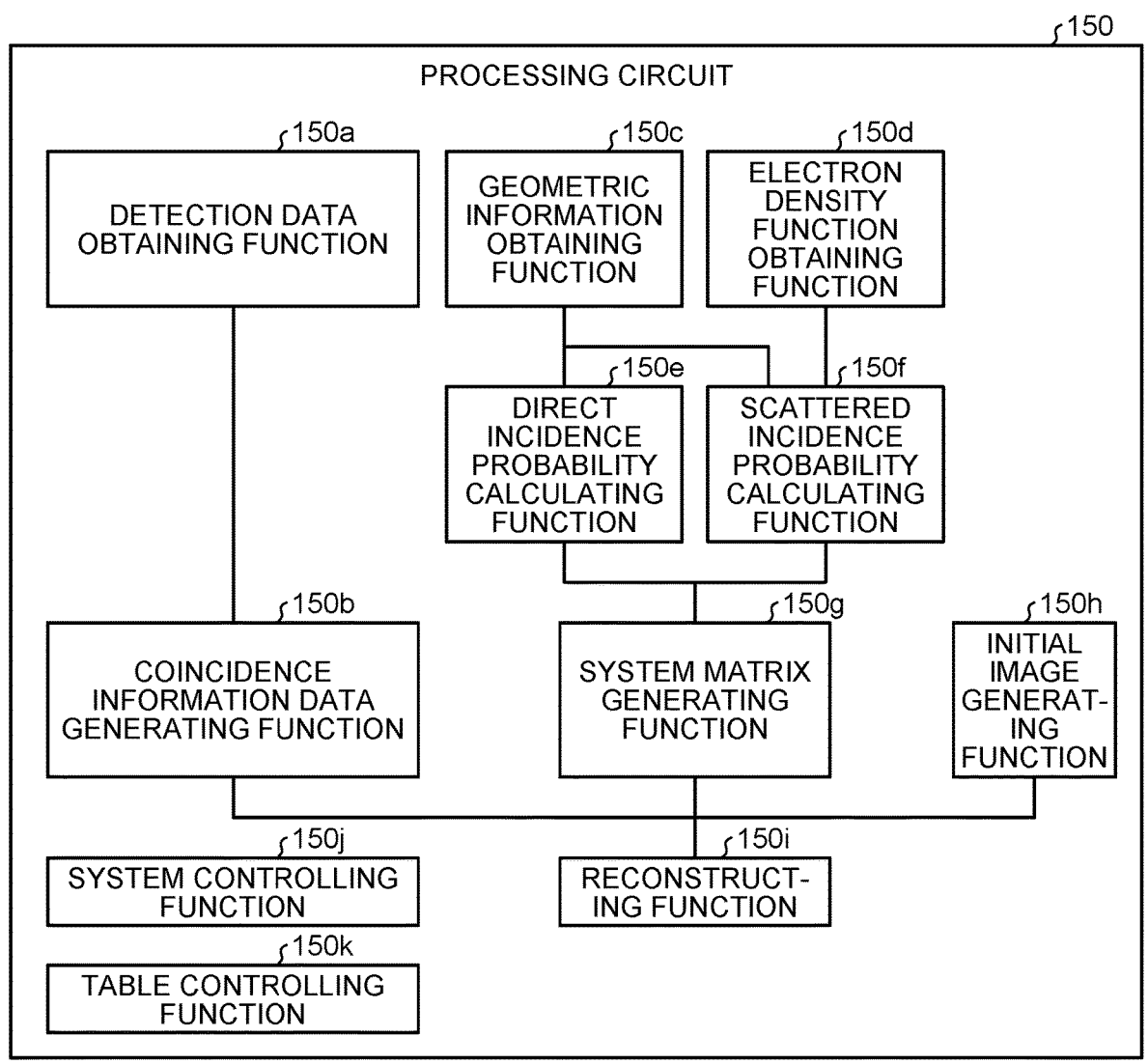
FIG. 5 is a diagram for explaining a processing circuit according to a second embodiment.

FIG. 5 illustrates a configuration of the processing circuit 150 according to the second embodiment. In FIG. 5, because the functions other than the direct incidence probability calculating function 150e are the same as those in the first embodiment, detailed explanations thereof will be omitted. In the first embodiment, as for the direct incidence probability calculating function 150e, the processing circuit 150 is configured to estimate the direct incidence probability by using both the geometric information of the detectors and the electron density function of the patient. In contrast, in the second embodiment, the processing circuit 150 is configured to estimate a direct incidence probability by using only the geometric information of the detectors.

Similarly to FIG. 3, in FIG. 5, the detection data obtaining function 150a, the coincidence information data generating function 150b, and the initial image generating function 150h are examples of the first obtaining unit. Further, the geometric information obtaining function 150c and the electron density function obtaining function 150d are examples of the second obtaining unit. The direct incidence probability calculating function 150e, the scattered incidence probability calculating function 150f, and the system matrix generating function 150g are examples of the estimating unit. The reconstructing function 150i is an example of the reconstructing unit. The system controlling function 150j and the table controlling function 150k are examples of a controlling unit.

Figure 6:
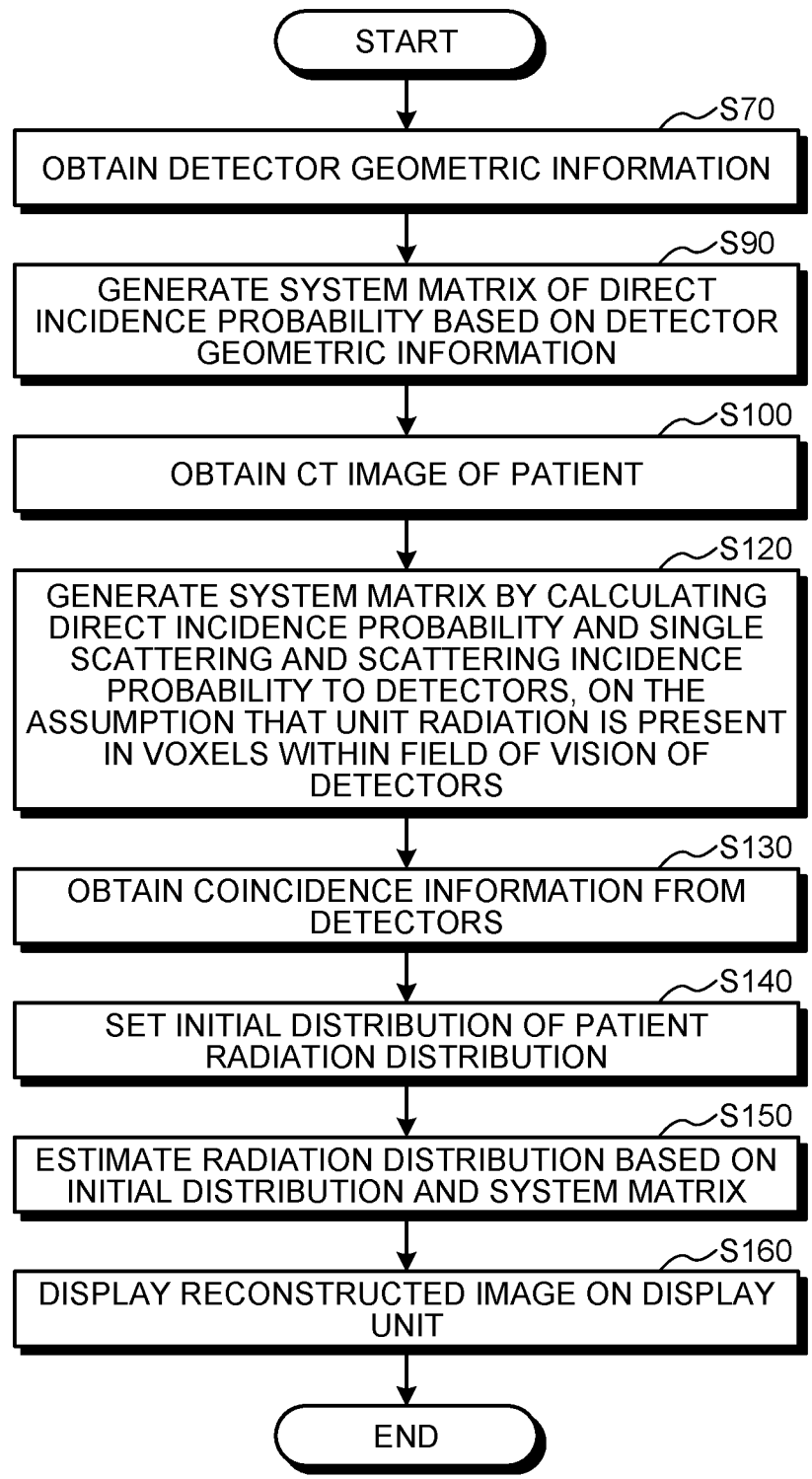
FIG. 6 is a flowchart for explaining a procedure in a process performed by a nuclear medicine diagnosis apparatus according to the second embodiment.

FIG. 6 illustrates a flow in a process performed by the PET apparatus 100 according to the second embodiment. In this situation, because the processes other than those at steps S70, S90, and S120 are the same as those in the first embodiment, duplicate explanations thereof will be omitted.

To begin with, at step S70, by employing the geometric information obtaining function 150c, the processing circuit 150 obtains detector geometric information. Although the process at step S70 is the same as the process at step S110 in the first embodiment, the process in the second embodiment is performed with the timing described herein.

Subsequently, at step S90, by employing the direct incidence probability calculating function 150e, the processing circuit 150 calculates a direct incidence probability serving as the first probability value, based on the detector geometric information obtained by the geometric information obtaining function 150c at step S70. In this situation, by employing the direct incidence probability calculating function 150e, the processing circuit 150 calculates the direct incidence probability serving as the first probability value, without using an electron density function of the patient. After that, at step S90, by employing the system matrix generating function 150g, the processing circuit 150 calculates, of the system matrix, a contribution corresponding to the direct incidence probability serving as the first probability value, based on the calculated first probability value. In other words, by employing the system matrix generating function 150g, the processing circuit 150 generates a system matrix of the direct incidence probability, based on the detector geometric information.

After that, at steps S100 and S110, the processing circuit 150 obtains an electron density function of the patient by employing the electron density function obtaining function 150d, by performing the same processes as those in the first embodiment.

Subsequently, at step S120, by employing the scattered incidence probability calculating function 150f, the processing circuit 150 calculates a scattered incidence probability serving as the second probability value, by performing the same process as that in the first embodiment. After that, by employing the system matrix generating function 150g, the processing circuit 150 generates a system matrix, based on the direct incidence probability that serves as the first probability value and was calculated in advance at step S90 and the scattered incidence provability that serves as the second probability value and was calculated at step S120 similarly to that in the first embodiment. Subsequently, at steps S130 through S160, the same processes as those in the first embodiment are performed.

As explained above, in the second embodiment, by employing the reconstructing function 150i, the processing circuit 150 is configured to reconstruct a PET image based on the system matrix based on the first probability value calculated in advance prior to obtaining the electron density function of the patient. As a result, of the system matrix, there is no need to calculate the direct incidence probability with respect to each patient. It is therefore possible to simplify the calculation of the system matrix. Consequently, it is possible to reduce calculation loads in the reconstructing process.

Third Embodiment

In the first and the second embodiments, the example was explained in which the effects of the scatterings are expressed as the scattering matrix while being incorporated in the values of the system matrix; however, possible embodiments are not limited to this example. In the third embodiment, an example will be explained in which a shifted Poisson model or the like is adopted, for example, so that the effects of the scatterings are expressed as the scattering term serving as a correction term for the system matrix.

Figure 7:
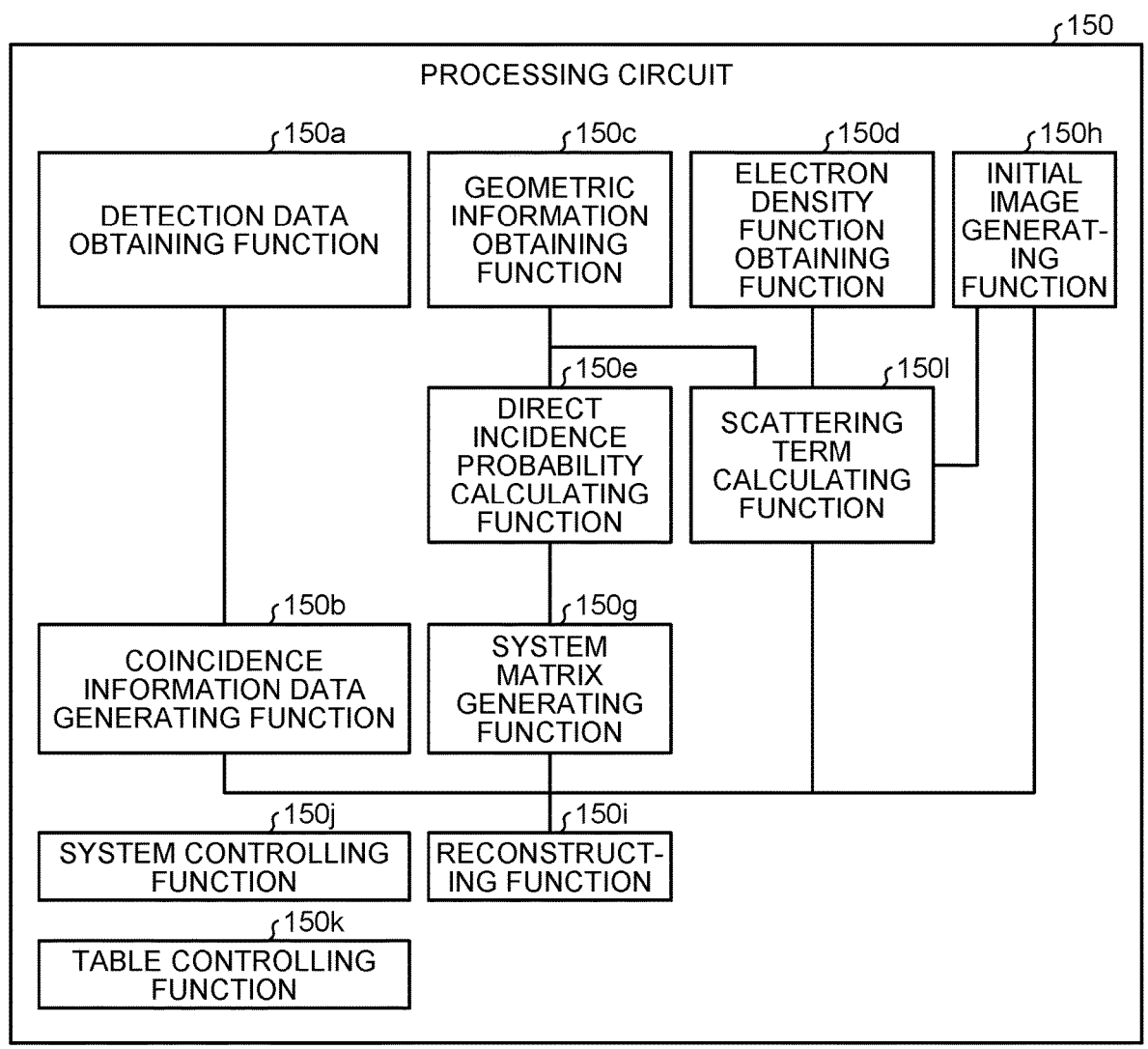
FIG. 7 is a drawing for explaining a processing circuit according to a third embodiment.

FIG. 7 illustrates a configuration of the processing circuit 150 according to the third embodiment. In FIG. 7, because the functions other than a scattering term calculating function 150*l* are the same as those in the second embodiment, detailed explanations thereof will be omitted.

In the present example, it is possible to express a scattering term $S_j$ calculated by the processing circuit 150 while employing the scattering term calculating function 150*l*, by using Expression (1) presented below, where the letter "j" is a subscript indicating a j-th LOR.

$$\lambda_i^{k+1} = \frac{\lambda_i^k}{\sum_j H_{ij}} \sum_j H_{ij} \frac{g_j}{\sum_m H_{mj}\lambda_m^k + S_j} \quad (1)$$

In Expression (1), the letters "i" and "m" are subscripts indicating an i-th voxel and an m-th voxel, respectively. The letter "k" is a subscript indicating a k-th iteration in the image reconstructing process. The element "$\lambda_i^k$" denotes an estimated value for a radiation value in the i-th voxel in the k-th iteration. The element "$H_{ij}$" denotes a system matrix between the i-th voxel and the j-th LOR. The element "$g_j$" denotes the number of events detected by the detectors in the j-th LOR. In other words, the scattering term $S_j$ calculated by the processing circuit 150 by employing the scattering term calculating function 150*l* is a parameter related to the scattered rays and is a correction term for the system matrix introduced for each LOR at the time of reconstructing a PET image.

In FIG. 7, the detection data obtaining function 150*a*, the coincidence information data generating function 150*b*, and the initial image generating function 150*h* are examples of the first obtaining unit. Further, the geometric information obtaining function 150*c* and the electron density function obtaining function 150*d* are examples of the second obtaining unit. The direct incidence probability calculating function 150*e*, the scattered incidence probability calculating function 150*f*, and the system matrix generating function 150*g* are examples of the estimating unit. The scattering term calculating function 150*l* is an example of the identifying unit. The reconstructing function 150*i* is an example of the reconstructing unit. The system controlling function 150*j* and the table controlling function 150*k* are examples of a controlling unit.

Figure 8:
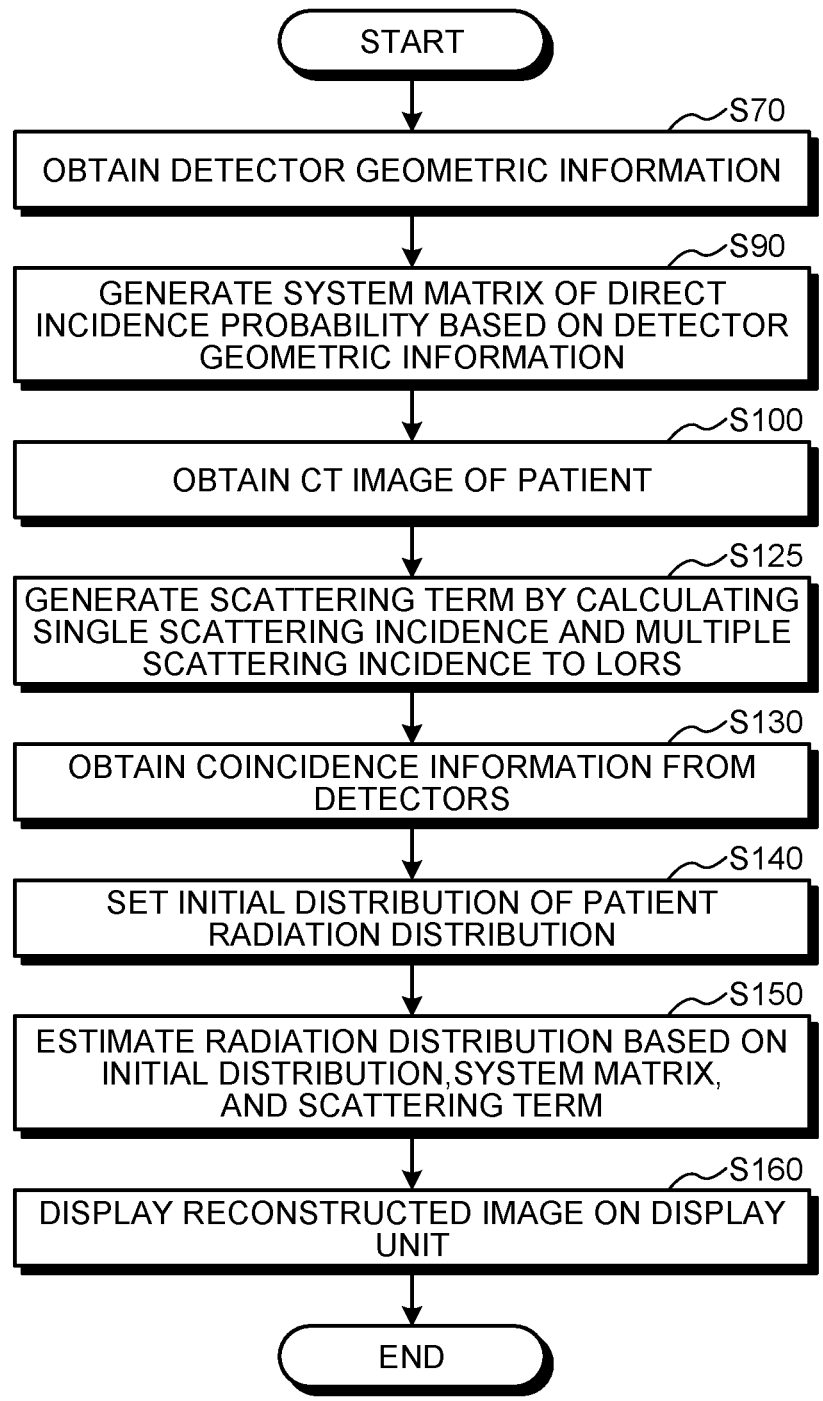
FIG. 8 is a flowchart for explaining a procedure in a process performed by a nuclear medicine diagnosis apparatus according to the third embodiment.

FIG. 8 illustrates a flow in a process performed by the PET apparatus 100 according to the third embodiment. In this situation, because the processes other than those at steps S90, S125 and S150 are the same as those in the second embodiment, duplicate explanations thereof will be omitted.

Similarly to the second embodiment, at step S90, by employing the direct incidence probability calculating function 150*e*, the processing circuit 150 estimates the direct incidence probability serving as the first probability value based on the detector geometric information obtained by the geometric information obtaining function 150*c* at step S70, so as to generate the system matrix based on the detector geometric information by employing the system matrix generating function 150*g*.

In this situation, unlike in the second embodiment in which the scatterings are incorporated in the components of the system matrix, the effects of the scattering in the third embodiment are expressed as the scattering term serving as the correction term for the system matrix and are therefore not the components of the system matrix. Accordingly, at step S90, the processing circuit 150 already generates the system matrix by employing the system matrix generating function 150*g*.

At step S125, by employing the scattered incidence probability calculating function 150*f*, the processing circuit 150 calculates the second probability which is a probability of the gamma rays becoming incident to the detectors after going through single scattering or multiple scatterings, based on the electron density of the patient obtained by the electron density function obtaining function 150*d* at step S100 and the geometric information of the detectors 1 obtained by the geometric information obtaining function 150*c* at step S70.

In other words, by employing the scattered incidence probability calculating function 150*f*, the processing circuit 150 estimates the second probability value corresponding to the scattering events including multiple scattering events in the patient, based on the electron density function of the patient and the geometric information of the gamma ray detectors. More specifically, by employing the scattered incidence probability calculating function 150*f*, the processing circuit 150 calculates the scattered incidence probability of the scattering events including the multiple scattering events, by using, for example, a radiative transfer equation, a Monte Carlo simulation, a neural network, or the like. Subsequently, by employing the scattering term calculating function 150*l*, the processing circuit 150 identifies the scattering term serving as the parameter related to the scattered rays, by performing the scattering calculation based on the detector geometric information obtained at step S70, the direct incidence probability that serves as the first probability value and was estimated at step S90, the electron density function of the patient obtained at step S100, and the initial estimated value for the radiation distribution of the patient. In this situation, the scattering term serving as the parameter related to scattering term includes a multiple scattering term.

Further, at step S150, by employing the reconstructing function 150*i*, the processing circuit 150 reconstructs a PET image, by estimating the value on the left-hand side of Expression (1) by evaluating the right-hand side of Expression (1), for example, and also estimating the radiation distribution of the patient, based on the initial estimated value of the radiation distribution of the patient set at step S140, the system matrix generated at step S90, and the scattering term that serves as the parameter related to the scattered rays and was generated at step S125.

In this situation, the data obtained by the processing circuit 150 while employing the electron density function obtaining function 150*d* at step S100, for example, does not necessarily have to be a CT image and may be a magnetic resonance image, for instance. In an example, by employing a segmentation function (not illustrated), the processing circuit 150 automatically extracts/determines sites by performing a segmentation process on the magnetic resonance image. After that, with respect to the magnetic resonance image, the processing circuit 150 converts magnetic resonance signal values into CT values for each of the extracted/determined sites, so as to generate a magnetic resonance image having signal values similar to those in a CT image. By employing the electron density function obtaining function 150d, the processing circuit 150 obtains the magnetic resonance image as an image indicating the electron density of the patient.

In another example, by employing the system matrix generating function 150g, the processing circuit 150 may identify a scattering region by performing, for example, a semantic segmentation process on the CT image of the patient obtained at step S100, so as to estimate a second probability value based on the identified scattering region. As a result, it is possible to reduce calculation loads involved in the image reconstructing process.

As explained above, in the third embodiment, by employing the scattering term calculating function 150l, the processing circuit 150 calculates the scattering term serving as the parameter related to the scattered rays while including the multiple scatterings, based on the detector geometric information and the electron density function, so as to reconstruct the PET image by using the system matrix calculated separately and the scattering term. In this manner, by performing the reconstructing process by calculating the term including the multiple scatterings as the scattering term separately from the system matrix, it is possible to perform the PET reconstructing process with a high level of precision on the data containing the scatterings including the multiple scatterings.

Fourth Embodiment

Next, a fourth embodiment will be explained. At the time of generating coincidence data, the coincidence data may be generated in some situations by eliminating noise while using a low-pass filter or a peak value discriminator (discriminator) on an output result from a gamma ray detector. In this situation, for example, the value of a parameter used by the peak value discriminator for a peak value cut-off may be different for each of the detectors. In the fourth embodiment, by reconstructing an image while using the value of the parameter used for the peak value cut-off with respect to each detector, it is possible to further enhance the image quality of the reconstructed PET image.

Figure 9:
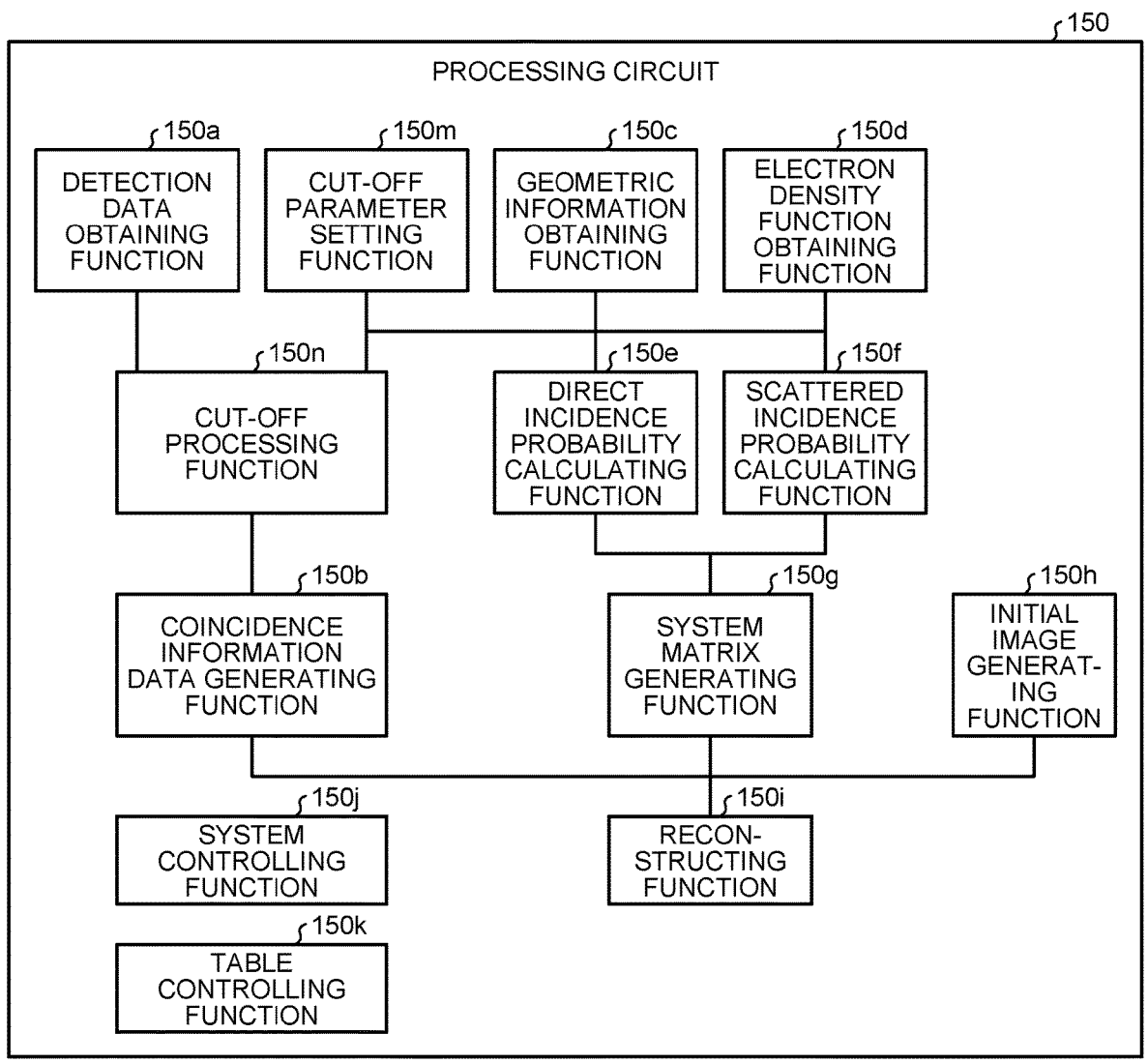
FIG. 9 is a drawing for explaining a processing circuit according to a fourth embodiment.

FIG. 9 illustrates a configuration of the processing circuit 150 according to the fourth embodiment. In FIG. 9, because the functions other than a cut-off processing function 150n and a cut-off parameter setting function 150m are the same as those in the first embodiment, detailed explanations thereof will be omitted.

The cut-off processing function 150n is a function configured to perform a noise cut process on the count data obtained by the detector data obtaining function 150a, by using a low-pass filter or a peak value discriminator (a discriminator). In an example, by employing the cut-off processing function 150n, the processing circuit 150 is configured to eliminate certain count data smaller than a prescribed peak value cut-off parameter, from the count data obtained by the gamma ray detector data obtaining function 150a, for example. When the count data obtained by the detector data obtaining function 150a is smaller than the prescribed peak value cut-off parameter, for example, the count data to be output is 0.

Further, by employing the cut-off parameter setting function 150m, the processing circuit 150 sets a value of the abovementioned cut-off parameter.

In FIG. 9, the detection data obtaining function 150a, the coincidence information data generating function 150b, the cut-off parameter setting function 150m, the cut-off processing function 150n, and the initial image generating function 150h are examples of the first obtaining unit. Further, the geometric information obtaining function 150c and the electron density function obtaining function 150d are examples of the second obtaining unit. The direct incidence probability calculating function 150e, the scattered incidence probability calculating function 150f, and the system matrix generating function 150g are examples of the estimating unit. The reconstructing function 150i is an example of the reconstructing unit. The system controlling function 150j and the table controlling function 150k are examples of a controlling unit.

FIG. 10 illustrates a flow in a process performed by the PET apparatus 100 according to the fourth embodiment. In this situation, because the processes other than those at steps S80, S85, S120, S130 and S150 are the same as those in the first embodiment, duplicate explanations thereof will be omitted.

At step S80, by employing the cut-off parameter setting function 150m, the processing circuit 150 sets a peak value cut-off parameter. Further, at step S130, similarly to the first embodiment, by employing the detection data obtaining function 150a, the processing circuit 150 obtains the gamma ray detection data as the count information from the timing information obtaining circuit 102. Subsequently, by employing the coincidence information data generating function 150b, the processing circuit 150 generates coincidence information data based on the count information obtained by the gamma ray detection data obtaining function 150a and the peak value parameter set at step S80. In other words, by employing the coincidence information data generating function 150b, the processing circuit 150 generates the coincidence data by applying the peak value cut-off to the output result from the gamma ray detector.

Further, at step S85, the processing circuit 150 notifies a scattered incidence calculating unit including the direct incidence probability calculating function 150e and the scattered incidence probability calculating function 150f or the like of the peak value cut-off parameter set at step S80.

Further, at step S120, the processing circuit 150 calculates a direct incidence probability by employing the direct incidence probability calculating function 150e and further calculates a scattered incidence probability based on the scattered incidence probability calculating function 150f; however, by employing the direct incidence probability calculating function 150e, the processing circuit 150 estimates a direct incidence probability as the first probability value, based on the value of the peak value parameter provided in the notification at step S85. Further, by employing the scattered incidence probability calculating function 150f, the processing circuit 150 estimates a scattered incidence probability as the second probability value, based on the value of the peak value parameter provided in the notification at step S85.

Further, by employing the system matrix generating function 150g, the processing circuit 150 generates a system matrix based on the direct incidence probability calculated by the direct incidence probability calculating function 150e and the scattered incidence probability calculated by the scattered incidence probability calculating function 150f; however, in this situation, the system matrix is generated based on the value of the peak value parameter provided in the notification at step S85. In other words, the processing circuit 150 causes the differences in the cut-off parameters among the detectors to be reflected in the system matrix generated at step S120.

Further, at step S150, by employing the image reconstructing function 150i, the processing circuit 150 generates a reconstructed image through reconstruction of a PET image, by estimating a radiation distribution of the patient based on the initial distribution of the patient radiation set at step S140, the system matrix generated at step S120, the coincidence data obtained at step S130, and the peak value parameter set by the cut-off parameter setting function.

As explained above, in the fourth embodiment, the scattering evaluating process and the image reconstructing process are performed by using the value of the parameter used for the peak value cut-off with respect to each of the detectors. It is therefore possible to further enhance the image quality of the reconstructed PET image.

According to at least one aspect of the embodiments described above, it is possible to enhance the image quality.

Regarding the embodiments described above, the following notes are disclosed as certain aspects and selected characteristics of the present disclosure.

Note 1:
A nuclear medicine diagnosis apparatus provided in one aspect of the present disclosure includes a first obtaining unit, a second obtaining unit, an estimating unit, and a reconstructing unit. The first obtaining unit is configured to obtain coincidence data including a direct incidence event to a gamma ray detector and a scattering event in a subject. The second obtaining unit is configured to obtain an electron density function of the subject and geometric information of the gamma ray detector. The estimating unit is configured to estimate a first probability value corresponding to the direct incidence event in the subject and a second probability value corresponding to the scattering event, based on one or both of the electron density function and the geometric information. The reconstructing unit is configured to reconstruct a PET image based on the first probability value, the second probability value, and the coincidence data.

Note 2:
The estimating unit may estimate the first probability value by using a radiative transfer equation, a Monte Carlo simulation, or a neural network.

Note 3:
The estimating unit may estimate the second probability value by using a radiative transfer equation, a Monte Carlo simulation, or a neural network.

Note 4:
The scattering event may include a multiple scattering event.

The reconstructing unit may reconstruct the PET image based on a system matrix based on the first probability value.

Note 5:
The reconstructing unit may reconstruct the PET image based on a system matrix based on the first probability value and the second probability value.

Note 6:
The estimating unit may estimate the first probability value based on the geometric information and may estimate the second probability value based on the geometric information and the electron density function.

Note 7:
An identifying unit configured to identify a parameter related to a scattered ray based on the geometric information and the electron density function may further be provided, and
the reconstructing unit may reconstruct the PET image based on the parameter.

Note 8:
The reconstructing unit may reconstruct the PET image by using a shifted Poisson model.

Note 9:
The first obtaining unit may generate the coincidence data by applying a peak value cut-off to an output result from the gamma ray detector, and
the estimating unit may estimate the first probability value and the second probability value based on a parameter used for the peak value cut-off.

Note 10:
The estimating unit may identify a scattering region by performing a segmentation process and may estimate the second probability value based on the identified scattering region. The segmentation process may be a semantic segmentation process.

Note 11:
The electron density function may be a CT image.

Note 12:
The electron density function may be generated based on a magnetic resonance image.

Note 13:
A medical image processing device provided in one aspect of the present disclosure includes a first obtaining unit, a second obtaining unit, an estimating unit, and a reconstructing unit. The first obtaining unit is configured to obtain coincidence data including a direct incidence event to a gamma ray detector and a scattering event in a subject. The second obtaining unit is configured to obtain an electron density function of the subject and geometric information of the gamma ray detector. The estimating unit is configured to estimate a first probability value corresponding to the direct incidence event in the subject and a second probability value corresponding to the scattering event, based on one or both of the electron density function and the geometric information. The reconstructing unit is configured to reconstruct a PET image based on the first probability value, the second probability value, and the coincidence data. The reconstructing unit is configured to reconstruct the PET image based on a system matrix that is based on the first probability value and the second probability value.

Note 14:
A nuclear medicine diagnosis method provided in one aspect of the present disclosure is a nuclear medicine diagnosis method that is implemented by a nuclear medicine diagnosis apparatus and includes: obtaining coincidence data including a direct incidence event to a gamma ray detector and a scattering event in a subject; obtaining an electron density function of the subject and geometric information of the gamma ray detector; estimating a first probability value corresponding to the direct incidence event in the subject and a second probability value corresponding to the scattering event, based on one or both of the electron density function and the geometric information; and reconstructing a PET image based on the first probability value, the second probability value, and the coincidence data. The method comprises reconstructing the PET image based on a system matrix that is based on the first probability value and the second probability value.

Note 15:

A program provided in one aspect of the present disclosure is configured to cause a computer to perform processes of: obtaining coincidence data including a direct incidence event to a gamma ray detector and a scattering event in a subject including a multiple scattering event; obtaining an electron density function of the subject and geometric information of the gamma ray detector; estimating a first probability value corresponding to the direct incidence event in the subject and a second probability value corresponding to the scattering event, based on one or both of the electron density function and the geometric information; and reconstructing a PET image based on the first probability value, the second probability value, and the coincidence data. The process comprises reconstructing the PET image based on a system matrix that is based on the first probability value and the second probability value.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnosis apparatus, comprising:
a processing circuit configured to:
    obtain coincidence data including a direct incidence event to a gamma ray detector and a scattering event in a subject, wherein the scattering event includes a multiple scattering event;
    obtain an electron density function of the subject and geometric information of the gamma ray detector;
    estimate a first probability value corresponding to the direct incidence event in the subject and a second probability value corresponding to the scattering event, based on one or both of the electron density function and the geometric information; and
    reconstruct a Positron Emission Tomography (PET) image based on the first probability value, the second probability value, and the coincidence data, wherein the processing circuit is further configured to reconstruct the PET image based on a system matrix that is based on the first probability value and the second probability value.

2. The nuclear medicine diagnosis apparatus according to claim 1, wherein the processing circuit is further configured to estimate the first probability value based on the geometric information and estimate the second probability value that is based on the geometric information and the electron density function.

3. The nuclear medicine diagnosis apparatus according to claim 1, where
the processing circuit is further configured to generate the coincidence data by applying a peak value cut-off to an output result from the gamma ray detector, and
the processing circuit is further configured to estimate the first probability value and the second probability value based on a parameter used for the peak value cut-off.

4. The nuclear medicine diagnosis apparatus according to claim 1, wherein the processing circuit is further configured to identify a scattering region by performing a segmentation process and estimate the second probability value based on the identified scattering region.

5. A nuclear medicine diagnosis apparatus, comprising:
a processing circuit configured to:
    obtain coincidence data including a direct incidence event to a gamma ray detector and a scattering event in a subject;
    obtain an electron density function of the subject and geometric information of the gamma ray detector;
    estimate a first probability value corresponding to the direct incidence event in the subject and a second probability value corresponding to the scattering event, based on one or both of the electron density function and the geometric information; and
    reconstruct a Positron Emission Tomography (PET) image based on the first probability value, the second probability value, and the coincidence data, wherein
the scattering event includes a multiple scattering event,
the processing circuit is further configured to reconstruct the PET image based on a system matrix that is based on the first probability value,
the processing circuit is further configured to identify a parameter related to a scattered ray based on the geometric information and the electron density function, and
the processing circuit is further configured to reconstruct the PET image based on the parameter.

6. A nuclear medicine diagnosis method implemented by a nuclear medicine diagnosis apparatus, the nuclear medicine diagnosis method comprising:
    obtaining coincidence data including a direct incidence event to a gamma ray detector and a scattering event in a subject, wherein the scattering event includes a multiple scattering event;
    obtaining an electron density function of the subject and geometric information of the gamma ray detector;
    estimating a first probability value corresponding to the direct incidence event in the subject and a second probability value corresponding to the scattering event, based on one or both of the electron density function and the geometric information; and
    reconstructing a Positron Emission Tomography (PET) image based on the first probability value, the second probability value, and the coincidence data, wherein the method further comprises reconstructing the PET image based on a system matrix that is based on the first probability value and the second probability value.

* * * * *